United States Patent [19]

Hara

[11] Patent Number: 4,958,281

[45] Date of Patent: * Sep. 18, 1990

[54] SIGNAL PROCESSING METHOD FOR DETERMINING BASE SEQUENCE OF NUCLEIC ACID

[75] Inventor: Makoto Hara, Kanagawa, Japan

[73] Assignee: Fuji Photo Film Co., Ltd., Kanagawa, Japan

[*] Notice: The portion of the term of this patent subsequent to Jan. 31, 2006 has been disclaimed.

[21] Appl. No.: 917,609

[22] Filed: Oct. 10, 1986

[30] Foreign Application Priority Data

Oct. 11, 1985 [JP] Japan ................... 60-226091

[51] Int. Cl.$^5$ ........................................... G01N 33/58
[52] U.S. Cl. .................... 364/413.01; 382/6; 435/6; 935/77
[58] Field of Search ............ 364/413.01, 413.25; 382/6; 935/77; 435/6

[56] References Cited

U.S. PATENT DOCUMENTS

| | | | |
|---|---|---|---|
| 4,706,192 | 11/1982 | Nasu et al. | 364/413.01 |
| 4,741,043 | 4/1988 | Bacus et al. | 364/413.13 |
| 4,777,597 | 10/1988 | Shiraishi et al. | 364/413.01 |
| 4,802,101 | 1/1989 | Hara | 364/413.01 |

FOREIGN PATENT DOCUMENTS

| | | | |
|---|---|---|---|
| 123943A1 | 1/1984 | European Pat. Off. | |
| 0115777 | 5/1984 | European Pat. Off. | 435/6 |
| 160948A2 | 2/1985 | European Pat. Off. | |

OTHER PUBLICATIONS

"A Different Approach to DNA Sequencing", Nature vol. 274, Jul. 6, 1978.

*Primary Examiner*—Jerry Smith
*Assistant Examiner*—Kim Thanh T. Bui
*Attorney, Agent, or Firm*—Sixbey, Friedman, Leedom & Ferguson

[57] ABSTRACT

A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:

(1) preparing at least two one-dimensional waveforms composed of signal position along the resolving direction and signal level for each band;
(2) detecting a position where signal level is maximum on one of the one-dimensional waveforms;
(3) comparing the signal level at said maximum position on the one-dimensional waveform with signal levels at the corresponding positions on one-dimensional waveforms adjacent thereto, to determine a maximum position on the one-dimensional waveform having the highest signal level to be a band position;
(4) detecting a subsequent position where signal level is maximum on said one-dimensional waveform having the band position; and
(5) repeating in order the steps (3) and (4) to thereby determine all band positions on the resolved rows.

10 Claims, 1 Drawing Sheet

SIGNAL PROCESSING METHOD FOR DETERMINING BASE SEQUENCE OF NUCLEIC ACID

BACKGROUND OF THE INVENTION

1. Field of the Invention

This invention relates to a signal processing method for determining base sequence of nucleic acids.

2. Description of the Prior Art

It is essential to obtain genetic information carried by organisms in order to make the function or replication mechanism of the organism clear in the field of molecualr biology which has been rapidly developed in recent years. Particularly, it is essential to determine base sequence of nucleic acids such as DNA (or DNA fragment; the same applies hereinbelow) which carries specific genetic information.

Maxam-Gilbert method and Sanger-Coulson method are known as typicaly methods for determining the base sequence of nucleic acids such as DNA and RNA. In the former Maxam-Glibert method, a group containing a radioactive isotope such as $^{32}P$ is attached to a chain molecule of DNA or a DNA fragment at one end to label it with the radioactive element and then the bond between the constitutional units of the chain molecule is base-specifically cleaved by a chemical reaction. A mixture of the resulting base-specific DNA cleavage products is resolved (developed) through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in certain positional relationships with the end of the radioactive element-attached chain molecule can be sequentially determined according to the visualized autoradiograph and the applied base-specific cleavage means. In this way, the sequence for all bases of the DNA specimen can be determined.

In the latter sanger-Coulson method, synthetic DNA products which are complementary to the chain molecule of DNA or DNA fragment and radioactively labeled, are base-specifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

For the purpose of carrying out the determination of the base sequence of nucleic acids simply with high accuracy in autoradiography, there are described in U.S. patent application Nos. 837,037 and 664,405 autoradiographic procedures which utilizr a radiation image recording and reproducing method using a stimulable phosphor sheet, in place of the above-mensioned conventional radiography using a radiosensitive material such as an X-ray film. The stimulable phosphor sheet comprises a stimulable phosphor and has such properties that when exposed to a radiation, the stimulable phosphor absorbs a portion of radiation energy and then emits light (stimulated emission) corresponding to the radiation energy stood therein upon excitation with an electromagnetic wave (stimulating rays) such as visible light or infrared rays. According to this method, exposure time can be greatly shortened and there is no fear of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to image.

The base sequence of the nucleic acids has been conventionally determined by visually judging individual resolved positions of the base-specific cleavage products or the base-specific synthetic products of radioactively labeled nucleic acid (hereinafter referred as to simply base-specific fragments of nucleic acid) on the autoradiograph and comparing them among the resolved rows thereof. Namely, the analysis of the autoradiograph is done by observing the visualized autoradiograph with eyes, and such visual analysis requires great amounts of time and labor.

Further, since the visual analysis of the autoradiograph varies or fluctuates owing to the skill of investigators, the results on the determination of the base sequece of nucleic acid vary depending on the investigators and the accuracy of information is limited to a certain extent.

In order to improve the accuracy of the information, there are proposed in U.S. patent application Nos. 568,877 and 730,034 methods for automatically determining the base sequence of DNA by obtaining the autoradiograph as digital signals and subjecting the digital signals to appropriate signal processing. The digital signals corresponding to the autoradiograph can be obtained either by visualizing the autoradiograph on a radiographic film and photoelectrically reading out the visible image on said film by means of reflected light or transmitted light when the conventional radiography is employed, or by directly reading out the stimulable phosphor sheet without the visualization of the autoradiograph when the radiation image recording and reproducing method is employed.

However, the resolved pattern obtained by resolving (developing) radioactively labeled substances on a support medium by electrophoresis or the like is liable to cause various distortion and noise. For instance, there are the curve and the inclination of resolved rows. When resolving conditions are insufficient in the course of resolution, the resolved rows themselves may be curved in zigzags. The resolved pattern is inclined as a whole, when the superposition of the support medium on the radiosensitive material or the stimulable phosphor sheet is not exact in the exposure operation during the ccourse of obtaining the autoradiograph. Further, digital signals which have information on the curved resolved rows or the inclined resolved pattern may be obtained, when setting of the radiosensitive material or the phosphor sheet is insufficient in the read-out operation.

It is highly desired to automatically determine the base sequence of nucleic acids with high accuracy through the signal processing of the digital signals corresponding to the autoradiograph, even when the resolved rows cause distortion or the obtained digital signals contain information on distorted resolved rows.

SUMMARY OF THE INVENTION

The present invention has found that the base sequence of nucleic acids can be automatically determined with easiness and high accuracy by suitably processing digital signals corresponding to the autoradiograph of the resolved pattern containing distorted rows.

The present invention provides a signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:

(1) preparing at least two one-dimensional waveforms composed of signal position along the resolving direction and signal level for each band;

(2) detecting a position where signal level is maximum on one of the one-dimensional waveforms;

(3) comparing the signal level at said maximum position on the one-dimensional waveform with signal levels at the corresponding positions on one-dimensional waveforms adjacent thereto, to determine a maximum position on the one-dimensional waveform having the highest signal level to be a band position;

(4) detecting a subsequent position where signal level is maximum on said one-dimensional waveform having the band position; and (5) repeating in order the steps (3) and (4) to thereby determine all band positions in the resolved rows.

The present invention further provides a signal processing method for determining the base sequence of nucleic acids by subjecting said digital signals corresponding to the autoradiograph to signal processing, which comprises steps of:

(1) preparing at least two one-dimensional waveforms composed of signal position along the resolving direction and signal level for each band;

(2) detecting positions where signal level is maximum in the corresponding regions on two or more one-dimensional waveforms;

(3) comparing the signal levels at said maximum positions with each other, to determine the maximum position having the highest signal level to be a band position;

(4) detecting positions where signal level is maximum in the corresponding successive regions on two or more adjacent one-dimensional waveforms including said one-dimensional waveform having the band position; and (5) repeating in order the steps (3) and (4) to thereby determine all band positions on the resolved rows.

According to the present invention, the base sequence of the nucleic acids can be simply determined with high accuracy by processing the digital signals corresponding to the autoradiograph of a resolved pattern which is formed by resolving a mixture of the base-specific fragments of a nucleic acid on a support medium, through an appropriate signal processing circuit having a function capable of tracing a resolved row, even when the resolved rows are distorted.

More in detail, even when the resolved rows formed on a support medium is not straight but curved, or even when the resolved pattern based on digital image data is inclined as a whole, the resolved rows can be exactly pursued on the image data by use of the fact that bands (resolved portions) on the resolved rows are in the form of rectangle longitudinal in the width direction of the support medium. That is, the resolved rows can be precisely traced while determining the positions of bands, by conducting detection of digital signals so as to obtain plural signals in the width direction of each band and subjecting the signals to appropriate signal processing such as comparison operational processing. By comparing the bands with one another among the resolved rows on the basis of the determined band positions, the base sequence of the nucleic acid can be simply determined with high accuracy.

DETAILED DESCRIPTION OF THE INVENTION

Figure 1:
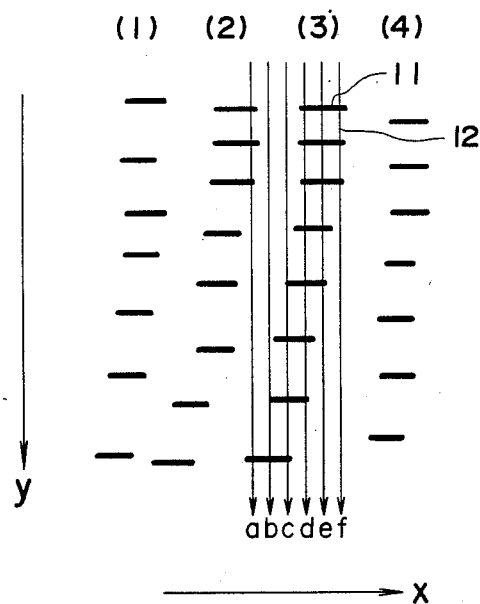
FIG. 1 is a partial view showing an example of a pattern in which electrophoretic rows cause distortion.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled labeled DNA according to the aforementioned Maxam-Gilbert method. A mixture of base-specific DNA synthetic products can be obtained by synthesizing from radioactively labeled deoxynucleoside triphosphates and DNA polymerase by use of DNA as a template according to the aforementioned Sanger-Coulson method.

Mixtures of base-specific RNA fragments can be also obtained as a mixture of cleavage products or a mixture of synthetic products in the similar manner to the DNA methods. DNA is composed of four kinds of bases: adenine, guanine, thymine and cytosine as its constitutional units, and RNA is composed of four kinds of bases: adenine, guanine, uracil and cytosine. These substances can be labeled with a radioactive element such as $^{32}P$, $^{14}C$, $^{35}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed by means of the conventional radiography using a radiosensitive material or the radiation image recording and reproducing method using a stimulable phosphor sheet. The digital signals corresponding to the autoradiograph are then obtained through an appropriate read-out system.

When the conventional radiography is used, the support medium and a radiosensitive material such as an X-ray film are placed together in layers at a low temperature of $-90°$ to $-70°$ C. for a long period of time (several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with an optical beam and the beam transmitted thereby or reflected therefrom is photoelectrically detected, whereby the visualized autoradiograph can be transformed to electric signals. Further, the electric signals are converted into digital signals corresponding to the autoradiograph through A/D conversion.

When the radiation image recording and reproducing method is used, the support medium and the stimulable phosphor sheet are placed together in layers at an ambient temperature for a short period of time (several seconds to several tens of minutes) to store radiation energy radiating from the radioactively labeled substances in the phosphor sheet, whereby the autoradiograph is recorded as a kind of a latent image (energy-stored image) on the phosphor sheet. The stimulable phosphor sheet, for instance, has a basic structure where a support port comprising a plastic film, a phosphor layer comprising a stimulable phosphor such as a divalent europium activated arium fluorobromide phosphor (BaFBr:$Eu^{2+}$) and a transparent protective film are lamicated in this order. The stimulable phosphor has characteristics of absorbing and storing radiation energy when irradiated with a radiation such as X-rays and subsequently releasing the stored radiaton energy as stimulated emission when excited with visible light to infrared rays.

Then, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization thereof. Further, the electric signals are converted into digital signals corresponding to the autoradiograph through A/D conversion.

The above-described methods for measuring the autoradiograph and obtaining the digital signals corresponding thereto are described in more detail in the aforementioned U.S. patent applications Nos. 837,037 and 568,877.

While the methods for obtaining the digital signals corresponding to the autoradiograph using the conventional radiography and the radiation image recording and reproducing method are described above, the present invention is not limited thereto and digital signals obtained by any other methods can be applied to the signal processing method of the invention, provided that they correspond to the autoradiograph.

In the above read-out procedures, it is not always necessary to conduct the read-out operation of the autoradiograph all over the surface of the radiographic film or the stimulable phosphor sheet. Only the image region may be subjected to the read-out operation.

In the present invention, there may be previously inputted information on the location of each resolved row and the width of band to preset read-out conditions and then conducted scanning at a scanning line density such that each band is traversed by at least two scanning lines in the read-out operation, so as to shorten read-out time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system fixed to the radiographic film or the stimulable phosphor sheet and a signal level (z) at the coordinate. The signal level represents the density of image at the coordinate, that is, the amount of the radioactively labeled substances. Accordingly, a series of the digital signals (namely, digital image data) have information on two-dimensional location of the labeled substances.

The digital signals corresponding to the autoradiograph of the radioactively labeled substances resolved on a support medium, is subjected to signal processing at determine the base sequence of nucleic acid according to the invention described in more detail below.

Now, the signal processing method of the present invention will be described by referring to an example of an electrophoretic pattern formed with a combination of the following four groups of base-specific DNA fragments labeled with a radioactive element:
(1) guanine (G)-specific DNA fragments,
(2) adenine (A)-specific DNA fragments,
(3) thymine (T)-specific DNA fragments,
(4) cystosine (C)-specific DNA fragments.

Each group of the base-specific DNA fragments is composed of base-specific cleavage products or synthetic products which have various lengths and the same base at terminals.

FIG. 1 partially shows an autoradiograph of the electrophoretic pattern obtained by electrophoresing the above four groups of the base-specific DNA fragments in four slots, respectively.

The digital signals corresponding to the autoradiograph are stored temporarily in a memory device of the signal processing circuit (that is, stored in a non-volatile memory unit such as a buffer memory, a magnetic disk, etc.).

In the first place, at least two one-dimensional waveforms are prepared for each band on each electrophoretic row (lane), and a position (peak position) where signal level is maximum is detected on an arbitrary one of the one-dimensional waveforms.

The one-dimensional waveform is a graph with position in the electrophoretic direction an abscissa and signal level as ordinate. When the detection of the digital signals are carried out by the scanning with a laser beam along each lane at such a scanning line density that at least two scanning lines traverse each band as described above (see: FIG. 1, wherein 11 is an electrophoretic band and 12 is a scanning line), the one-dimensional waveform composed of position (y) and signal level (z) can be directly prepared for every scanning line. When the autoradiograph is read out all over the surface, the similar scanning is conducted on the digital image data to extract signals along each lane and there are prepared the one-dimensional waveforms.

Figure 2:
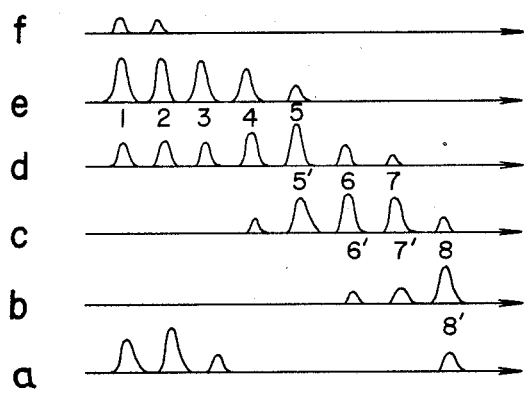
FIG. 2 is a partial view showing one-dimensional waveforms for the third slot.

FIG. 2 partially shows one-dimensional waveforms a to f for the third slot. The waveforms represent a cross-sectional image obtained when bands are cut off along the electrophoretic direction.

In FIG. 2, a peak position 1 is detected on the one-dimensional waveform e of the third slot. The peak position can be found out, for instance, by detecting a position where a sign of difference in signal level is inverted.

In the second place, the signal level at the peak position 1 on the waveform e is compared with signal levels at the corresponding positions on other one-dimensional waveforms adjacent to the waveform e (for instance, both the neighboring waveforms d and f). The term "corresponding position" means a position which stands at a migration distance equal to that of the peak position 1 or an extremely narrow region which stands close to and around the peak position 1. The peak position 1 on the waveform e, which has the highest signal level, is determined to be a band position.

In the third place, a position (peak position) 2 where signal level is maximum, being subsequent to the peak position 1, is detected on the waveform e containing the determined band position. In the same manner as described above, the signal level at the peak position 2 is compared with signal levels at the corresponding positions on the neighboring waveforms d and f, and the peak position 2 on the waveform e having the highest level is determined to be a nest band position.

The operations for the detection of the peak position on a one-dimensional waveform and the determination of the band position are repeatedly made until no more peak position is detected on one waveform. For instance, signal level at the peak position 5 on the waveform e is compared with signals levels at the corresponding positions on the adjacent waveforms c and d. When the signal level of the waveform d is the highest, it is estimated that a band position to be determined exists on the waveform d so that a new peak position 5' is detected on the waveform d and determined as a band position. The subsequent detection of a peak position is made on the waveform d. In this way, the band positions are determined in order of 1, 2, 3, 4, 5', 6', 7', . . . in FIG. 2.

Namely, by pursuing one-dimensional waveforms having higher signal level at the individual positions in order, a lane can be traced exactly without turning away therefrom, even when the lane is curved or inclined. By determining positions of bands on these one-dimensional waveforms, the band positions can be accurately obtained.

In the case that the detection of the digital signals is done by previously scanning the autoradiograph along the electrophoretic direction at an appropriate scanning density, the detection of a peak position on a one-dimensional waveform means to find out a position having a peak level along the scanning line.

Alternatively, the detection of the peak position may be simultaneously conducted on plural (e.g. two or three) one-dimensional waveforms adjacent to one another.

Peak positions are detected in the corresponding regions (extremely narrow regions which stand at an equal migration distance) of these one-dimensional waveforms. The signal levels at the peak position are compared with each other, and a peak position having the highest level is determined to be a band position.

Subsequently, peak positions are again detected in extremely narrow regions next to the above regions on adjacent one dimensional waveforms centering the waveform having the determined band position. A peak position having the highest level among them is determined to be a subsequent band position.

The operations for the detection of the peak positions on plural one-dimensional waveforms and the determination of the band position are repeatedly made until no more peak position is detected, whereby the positions of all bands on a lane can be determined. In this way, the band positions can be accurately determined by tracing the lane, while detecting the peak positions simultaneously on the plural one-dimensional waveforms and comparing them with each other.

The comparison of signal levels among the plural one-dimensional waveforms can be facilitated by subjecting the digital signals to threshold processing before the above-described operations.

Other lanes are also subjected to the above-described operations to determine the positions of all bands on the electrophoretic pattern.

Thus, the position of each band can be accurately determined by tracing each lane precisely, even when the lanes are curved or inclined.

When the electrophoretic pattern causes a smiling phenomenon, various distortions such as offset distortion and combining of some bands, or noise, signal processing for correction thereof may be made before or after the detection of the band positions is made.

The smiling phenomenon is a phenomenon in which migration distances of the radioactively labeled substances at the both sides of the support medium are shorter than that in the vicinity of the center thereof. The smiling phenomenon is caused by heat dissipation effect (so-called edge effect), etc. during the electrophoresis. The offset distortion is a phenomenon in which positions of the lanes are wholly deviated from one another and is caused by difference between the slots in the electrophoresis-starting position or time of samples, which is due to the unevenness of the shapes of slots, etc. The combining of bands is a phenomenon in which two or three bands are combined together to form one broad band and is caused by the insufficient electrophoresis. Usually, the combined bands tend to be appeared in the upper region of the pattern near the electrophoresis-starting position.

The signal processing methods for the correction for the smiling phenomenon, the offset distortion and the combining of bands are described in our co-pending Japanese Patent Applications Nos. 60(1985)-74899, No. 60(1985) -75900, No. 60(1985)-85275, No. 60(1985)-85276, No. 60 (1985)-111185 and No. 60(1985)-111186 (the whole content of which corresponds to U.S. patent application Nos. 849,187, 854,381 and No. ).

All the bands are sequenced immediately by comparing the resulting band positions with one another. The sequence can be easily determined by utilizing the fact that there do not exist two or more bands at the corresponding positions on different lanes, since the combination of the above four groups of the base-specific DNA fragments is exclusive. Since the slots (1) to (4) have information on the terminal bases of (G), (A), (T) and (C), respectively, the base sequence of DNA is obtained by substituting the bands with bases corresponding to the slots which the individual bands belong to. For instance, the following base sequence of DNA can be obtained.

A-G-C-T-A-A-G-. . .

Thus, the base sequence of one chain molecule of DNA can be determined. The representation mode of the information on the base sequence of DNA is by no means limited to the above-mentioned mode, and other representation modes may be utilized. For instance, the intensity ($z'$) of each band can be represented as the relative amount of the radioactively labeled substances, if desired. Further, the base sequence of both two chain molecules of DNA can be also represented.

Information on the base sequence of DNA can be also displayed as an image on the basis of the above processed digital signals. At the same time, the original autoradiograph can be displayed as a visible image. In this case, investigators themselves can finally determine the DNA sequence on the basis of the display image.

In the above-mentioned example, there has been described the case where the exclusive combination of the mixture (G, A, T, C) of base-specific DNA fragments as a sample is used, but the signal processing method of the present invention is by no means limited to said combination, and other combinations can be used. For instance, a combination of (G, G+A, T+C, C) may be used. Further, the signal processing method of the present invention can be also applied to the mixtures (for instance, a combination of G, A, U, C) of base-specific RNA fragments. The trace of lanes is not limited to resolved rows of one combination of base-specific fragments of a nucleic acid, but can be made for the whole resolved rows simultaneously resolved on a support medium.

It is possible to performs the genetic philological information processing such as comparison between the obtained base sequence of the DNA and the base sequence of another DNA which has been already recorded and stored in a suitable means.

The information on the base sequence of DNA determined through the above-described signal processing is output from the signal processing circuit and subsequently transmitted to a recording device directly or optionally via storage in a storing means such as a magnetic disk or a magnetic tape.

Various recording devices based on various systems can be employed for the above-mentioned purpose, for instance, a device for visualizing optically by scanning a photosensitive material with laser beam, etc., a display means for visualizing electrically on CRT, etc., a means for printing a radiation image displayed on CRT by means of a video printer, and a means for visualizing on a heatsensitive recording material using thermic rays.

I claim:

1. A signal processing method for determining base sequence of nucleic acids by subjecting digital signals to signal processing, said digital signals corresponding to an autoradiograph of plural distorted resolved rows which are formed by resolving a mixture of base-specific DNA fragments or base-specific RNA fragments labeled with a radioactive element in a one-dimensional resolving direction on a support medium, which comprises the steps of:
   (1) preparing at least two one-dimensional waveforms composed of signal position along the resolving direction and signal level for each band;
   (2) detecting a position where the signal level is maximum on one of the one-dimensional waveforms;
   (3) comparing the detected maximum signal level position on the one one-dimensional waveform with signal levels at corresponding positions on adjacent one-dimensional waveforms to determine a maximum position on the one-dimensional waveform having the highest signal level to be a band position;
   (4) detecting a subsequent position where the signal level is maximum on said one-dimensional waveform having the band position; and
   (5) repeating in order the steps (3) and (4) to thereby determine all band positions on the resolved rows.

2. The signal processing method as claimed in claim 1, wherein said digital signals are obtained by scanning the autoradiograph at a scanning line density that each band is traversed by at least two scanning lines, and in the step (1), said one-dimensional waveforms are prepared for each scanning line.

3. The signal processing method as claimed in claim 1, wherein the mixture of the base-specific DNA fragments consists of the four groups of:
   (1) guanine-specific DNA fragments;
   (2) adenine-specific DNA fragments;
   (3) thymine-specific DNA fragments; and
   (4) cytosine-specific DNA fragments;
and the resolved rows consist of four rows formed by resolving each of said four groups of the base-specific DNA fragments on the support medium.

4. The signal processing method as claimed in claim 1, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

5. The signal processing method as claimed in claim 1, wherein said digital signals corresonding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

6. A signal processing method for determining base sequence of nucleic acids by subjecting digital signals to signal processing, said digital signals corresponding to an autoradiograph of plural distorted resolved rows which are formed by resolving a mixture of base-specific DNA fragements or base-specific RNA fragments labeled with a radioactive element in a one-dimensional resolving direction on a support medium, which comprises the steps of:
   (1) preparing at least two one-dimensional waveforms composed of signal position along the resolving direction and signal level for each band;
   (2) detecting positions where the signal level is maximum in corresponding regions on two or more one-dimensional waveforms;
   (3) comparing the signal levels at said maximum positions with each other to determine the maximum position having the highest signal level to be a band position;
   (4) detecting positions where the signal level is maximum in the corresponding successive region on two or more adjacent one-dimensional waveforms including said one-dimensional waveform having the band position; and
   (5) repeating in order the steps (3) and (4) to thereby determine all band positions on the resolved rows.

7. The signal processing method as claimed in claim 6, wherein said digital signals are obtained by scanning the autoradiograph at a scanning line density that each band is traversed by at least two scanning lines, and in the step (1), said one-dimensional waveforms are prepared for each scanning line.

8. The signal processing method as claimed in claim 6, wherein the mixture of the base-specific DNA fragments consists of the four groups of:
   (1) guanine-specific DNA fragments;
   (2) adenine-specific DNA fragments;
   (3) thymine-specific DNA fragments; and
   (4) cytosine-specific DNA fragments;

and the resolved rows consist of four rows formed by resolving each of said four groups of the base-specific DNA fragments on the support medium.

9. The signal processing method as claimed in claim 6, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

10. The signal processing method as claimed in claim 6, wherein said digital signals corresponding to the autoradiograph are obtained by placing the support medium and a radiosensitive material together in layers to record the autoradiograph of the plural resolved rows on the radiosensitive material a a visible image and photoelectrically reading out the autoradiograph visualized on said radiosensitive material.

* * * * *